(12) United States Patent
d'Ussel

(10) Patent No.: US 6,663,591 B1
(45) Date of Patent: Dec. 16, 2003

(54) DISPOSABLE SAFETY SYRINGE

(76) Inventor: Bernard d'Ussel, 37 bd Latour-Maubourg, 75007 Paris (FR)

( * ) Notice: Subject to any disclaimer, the term of this patent is extended or adjusted under 35 U.S.C. 154(b) by 0 days.

(21) Appl. No.: 09/926,275

(22) PCT Filed: Apr. 13, 2000

(86) PCT No.: PCT/FR00/00951
§ 371 (c)(1), (2), (4) Date: Jan. 24, 2002

(87) PCT Pub. No.: WO00/61210
PCT Pub. Date: Oct. 19, 2000

(30) Foreign Application Priority Data

Apr. 14, 1999 (FR) .............................. 99 04630

(51) Int. Cl.⁷ ................................ A61M 5/00
(52) U.S. Cl. ...................... 604/110; 604/187
(58) Field of Search ............... 604/82, 87, 88, 604/110, 115, 117, 121–123, 134–139, 157–159, 164.11, 164.12, 167.03, 181, 165.01–165.04, 182, 186, 187, 188, 190–192, 195, 196, 198, 184, 218, 236, 239, 246, 247, 272, 411–416

(56) References Cited

U.S. PATENT DOCUMENTS

| | | | |
|---|---|---|---|
| 4,747,834 A | * | 5/1988 | Prindle ................. 604/184 |
| 4,857,061 A | | 8/1989 | Miller |
| 5,045,062 A | | 9/1991 | Henson |

FOREIGN PATENT DOCUMENTS

| | | |
|---|---|---|
| FR | 2 632 190 | 1/1989 |
| WO | WO 89/03698 | 5/1989 |
| WO | WO 91/12038 | 8/1991 |

* cited by examiner

Primary Examiner—Brian L. Casler
Assistant Examiner—Kevin C. Sirmons
(74) Attorney, Agent, or Firm—Jacobson Holman PLLC

(57) ABSTRACT

A disposable safety syringe including a cylindrical pump body extended by a needle integral with the body and including a plunger. The pump body includes a distal part provided with the needle and a proximal part with a larger diameter including the plunger; the distal part includes a sealing part.

4 Claims, 1 Drawing Sheet

DISPOSABLE SAFETY SYRINGE

This is a nationalization of PCT/FR00/00951 filed Apr. 13, 2000 and published in French.

FIELD OF THE INVENTION

The present invention relates to a disposable so-called safety syringe.

BACKGROUND OF THE INVENTION

Disposable syringes that must be discarded after use have been developed to prevent contamination: such syringes generally includes a pump body attached to the needle protected by a sheath before use. However, it has been realized that it is possible to refill these syringes and therefore to reuse them, whence serious risks of contamination.

One example of a disposable hypodermic syringe is described in U.S. Pat. No. 5,045,064. The syringe described includes valve means consisting of a stud mobile along a threaded shaft, a diaphragm between the stud and the needle. During an injection, the liquid to be injected, pushed by the plunger, entrains the stud by rotation along the diaphragm which traps it but allows the liquid to pass through it.

The syringe can therefore be used again if the stud does not cooperate with the diaphragm.

SUMMARY OF THE INVENTION

So, one aim of the present invention is to provide a disposable so-called safety syringe that cannot be refilled after it is first used.

Another object of the invention is to provide a syringe of this kind which can be manufactured easily and at lower additional cost compared to existing disposable syringes.

The above objects, and others that will become apparent hereinafter, are achieved by a disposable so-called safety syringe including a cylindrical pump body which is extended by a needle fastened to the body and which includes a plunger and a distal part fitted with the needle and a proximal part of larger diameter including a the plunger, the distal part including valve means, characterized in that the valve means comprise, on the one hand, a fixed member fastened to the inside wall of the distal part and a mobile member between the fixed member and the outlet from the proximal part into the distal part, the mobile member consisting of a valve connected by a compression leaf spring one end of which is fastened to the base of the valve and the other end of which is fastened to the inside wall of the distal part of the pump body.

The fixed member advantageously consists of at least one abutment fastened to the inside wall of the distal part of the pump body.

In a preferred embodiment of the invention the fixed member includes at least two abutments regularly distributed on a common circle and fastened to the inside wall of the distal part.

The valve is advantageously of cylindrical-conical shape, the conical part being directed towards the proximal part of the pump body and the cylindrical part including the propulsion means such as fins disposed at its periphery.

BRIEF DESCRIPTION OF THE DRAWINGS

The following description, which is not limiting on the invention, must be read in conjunction with the accompanying drawings, in which.

DETAILED DESCRIPTION OF THE PREFERRED EMBODIMENTS

Figure 1:
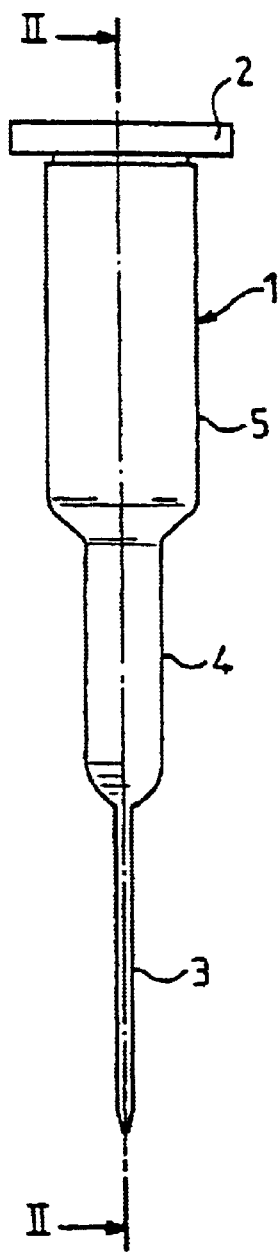
FIG. 1 is a plan view of a disposable so-called safety syringe in accordance with the present invention.

As can be seen in the figures, a syringe includes a cylindrical pump body 1 fitted with a plunger 2 and a needle 3 fastened to the pump body 1.

The pump body 1 has a distal part 4 carrying the needle 3 and a proximal part 5 of larger diameter containing the plunger 2; the distal part 4 includes valve means.

The skilled person is aware that "distal" refers to any part at the needle end and "proximal" refers to any part at the plunger end.

The valve means comprise, on the one hand, a fixed member 6 fastened to the inside wall of the distal part 4 and a mobile member 7 that can move between this fixed member 6 and the outlet 8 of the proximal part 5 into the distal part 4.

The fixed member 6 consists of at least one abutment fastened to the inside wall of the distal part 4 of the pump body 1. In a preferred embodiment, the fixed member 6 consists of two abutments 6a and 6b disposed symmetrically on a common circle on the inside wall of the distal part 4.

In accordance with the present invention, the mobile member 7 consists of a valve connected by pressure means 9 to the inside wall of the distal part 4. The valve is of cylindrical-conical shape, the conical part 7a being directed towards the proximal part 5 of the pump body 1 and the cylindrical part 7b including propulsion means such as fins 10 disposed at its periphery.

The pressure means preferably consist of a leaf spring 9 one end of which is fastened to the base of the mobile member 7 and the other end of which is fastened to the inside wall of the distal part 4 of the pump body 1, for example in the vicinity of the fixing of the needle 3 therein: the leaf spring is of the compression type.

Figure 2:
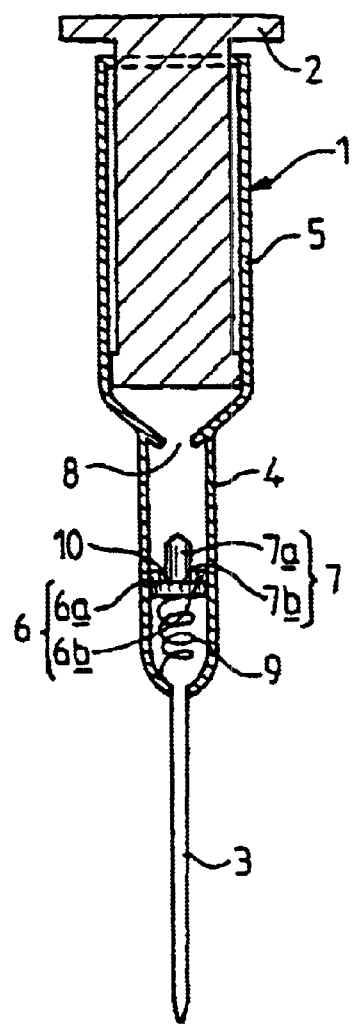
FIG. 2 is a view in section taken along the line II—II in FIG. 1, before any use of the syringe.
Figure 3:
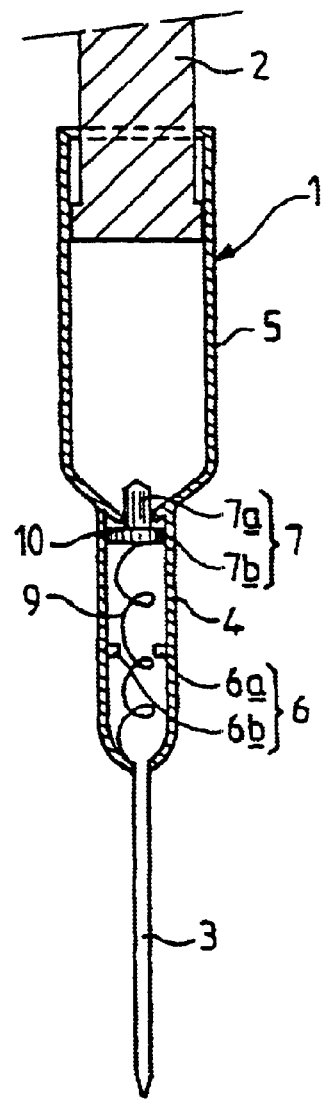
FIG. 3 is a view in section taken along the line II—II in FIG. 1 after filing the syringe.

When the syringe is empty, the mobile member 7 is held in position by the fins 10 cooperating with the abutments 6a and 6b, as shown in FIG. 2, the leaf spring holding the mobile member 7 pressed against the abutments. On actuating the plunger 2 to fill the syringe, the aspirated liquid enters the needle 3 through the distal part 4 without lifting the mobile member 7 off the abutments 6a and 6b which form a seat, due in particular to the shape of the fins 10, so that it is able to enter the proximal part 5 to the required level.

During injection, the liquid pushed by the plunger 2 creates a flow that exerts on the fins 10 of the mobile member 7 a force propelling the mobile member from the outlet of the proximal part 5 into the distal part 4, the leaf spring 9 also contributing to this same movement. The thrust of the plunger 2 nevertheless remains sufficiently high to counterbalance positively the propulsion force exerted on the mobile member 7.

When the injection is completed, the mobile member 7 is pressed against the outlet from the distal part 4 into the proximal part 5 by the leaf spring 9, and is held pressed against it: it is therefore impossible to aspirate a liquid and thereby reuse a syringe in accordance with the present invention.

What is claimed is:

1. A disposable safety syringe comprising: a cylindrical pump body extended by a needle fastened to said body including a plunger and a distal part fitted with said needle and a proximal part of larger diameter including said plunger, said distal part including a valve assembly for limiting use of the syringe to a single use, said valve assembly comprises, a fixed member fastened to an inside wall of the distal part and a mobile member located between said fixed member and an outlet from the proximal part into said distal part, said mobile member consisting of a valve connected by a compression leaf spring having two ends, one end of the compression spring being fastened to a base of said valve and the other end of the compression spring being fastened to the inside wall of said distal part of the pump body.

2. A syringe according to claim 1, wherein the fixed member consists of at least one abutment fastened to the inside-wall of the distal part of the pump body.

3. A syringe according to claim 2, wherein the fixed member includes at least two abutments regularly distributed on a common circle and fastened to the inside wall of the distal part.

4. A syringe according to claim 3, wherein the valve assembly is of cylindrical-conical shape, a conical part bing directed towards the proximal part of the pump body and a cylindrical part including fins disposed at its periphery.

* * * * *